US009879040B2

(12) United States Patent
Arlt

(10) Patent No.: US 9,879,040 B2
(45) Date of Patent: Jan. 30, 2018

(54) METATHESIS CATALYST

(71) Applicant: Dieter Arlt, Rinteln (DE)

(72) Inventor: Dieter Arlt, Rinteln (DE)

( * ) Notice: Subject to any disclaimer, the term of this patent is extended or adjusted under 35 U.S.C. 154(b) by 0 days.

(21) Appl. No.: 15/452,839

(22) Filed: Mar. 8, 2017

(65) Prior Publication Data

US 2017/0260220 A1 Sep. 14, 2017

(30) Foreign Application Priority Data

Mar. 8, 2016 (DE) .......................... 10 2016 002 694

(51) Int. Cl.
| | |
|---|---|
| *C07F 15/00* | (2006.01) |
| *C07B 37/08* | (2006.01) |
| *C08F 236/12* | (2006.01) |
| *B01J 31/22* | (2006.01) |

(52) U.S. Cl.
CPC ......... *C07F 15/0046* (2013.01); *B01J 31/223* (2013.01); *B01J 31/2291* (2013.01); *B01J 31/2295* (2013.01); *C07B 37/08* (2013.01); *C08F 236/12* (2013.01); *B01J 2231/543* (2013.01); *B01J 2531/821* (2013.01)

(58) Field of Classification Search
CPC .................................................. C07F 15/0046
See application file for complete search history.

(56) References Cited

U.S. PATENT DOCUMENTS

2013/0079575 A1 * 3/2013 Schertzer .................. C07C 6/04
585/510

* cited by examiner

*Primary Examiner* — Joseph R Kosack
(74) *Attorney, Agent, or Firm* — The H.T. Than Law Group

(57) ABSTRACT

The current invention describes new metathesis catalysts, a method for their preparation and their use in metathesis reactions.

2 Claims, No Drawings

METATHESIS CATALYST

The current invention describes new metathesis catalysts, a method for their preparation and their use.

BACKGROUND

Numerous metathesis catalysts are already known; refer to for example: Tetrahedron Lett. 1999, 40, 1091-1094, J. Am. Chem. Soc. 2000, 122, 58-71, Angew. Chem. 2003, 115, 1944-1968. It is known from these publications that substrates comprising acetal-groups considerably inhibit metathesis reactions.

DESCRIPTION

New metathesis catalysts comprising acetal-groups with the formula (I) have been found in which

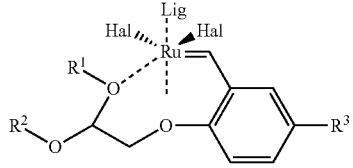
(I)

Ru stands for ruthenium,
R1 stands for alkyl,
R2 stands for alkyl,
R3 stands for hydrogen or for an electron-withdrawing substituent,
Hal stands for chlorine or bromine, independently of each other,
Lig stands for the ligand Lig1 or Lig2.

It was further found that the catalysts of formula (I) can be produced from compounds of formula (II)

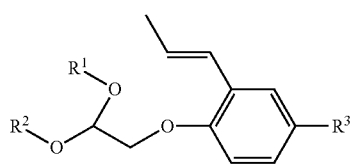
(II)

In which R1, R2 and R3 have the above given meanings, by reaction with $2^{nd}$ generation Grubbs catalyst (see Aldrich Chemistry Handbook Fine Chemicals 2009-2010, page 1453) in the presence of CuCl (J. Org. Chem. 2004, 69, 6894-6896).

It was finally found out that the catalysts of formula (I) are suitable for the modification of butadiene acrylonitrile copolymers.

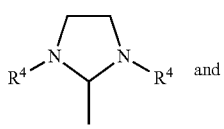
Lig1
and

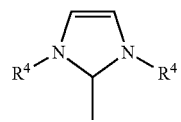
Lig2 wherein
R4 stands for mesityl.
Especially preferred are catalysts of formula (I), in which
R1 stands for methyl or ethyl,
R2 stands for C6-C18 alkyl,
R3 stands for hydrogen or C1-C18 alkyl or stands for an electron-withdrawing substituent from the series nitro and SO2N(C1-C18 alkyl),
Hal stands for chlorine or bromine, independently of each other,
Lig stands for

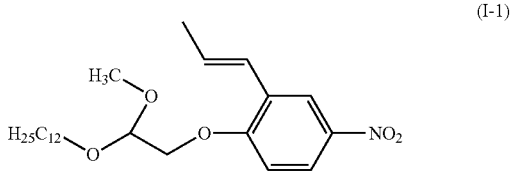

wherein
R4 stands for mesityl.

First Exemplary Embodiment

Preparation of the catalyst of formula (I), wherein R1=Me, R2=C12H25, R3=NO2, Hal=Cl, Lig=Lig1.

(I)

In a Schlenk apparatus, the $2^{nd}$-generation Grubbs catalyst (0.108 g, 0.13 mmol) is mixed with a solution of compound (I-1):

(I-1)

(0.059 g, 0.14 mmol) in 5 ml dichloromethane and 25 mg of copper-(I)-chloride and was stirred for about 50 minutes to about 60 minutes at ambient temperature under an argon atmosphere. The solvent was then removed under vacuum and the residue was purified by column chromatography. The catalyst (I) was obtained as a green solid.

Second Exemplary Embodiment

Preparation of the catalyst of formula (I), wherein R1=Me, R2=C12H25, R3=NO2, Hal=Cl, Lig=Lig1.

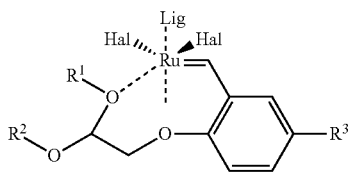

(I)

In a Schlenk apparatus, the 2$^{nd}$-generation Grubbs catalyst (0.108 g, 0.13 mmol) is mixed with a solution of compound (I-1):

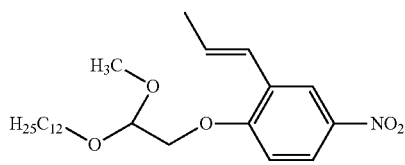

(I-1)

(0.059 g, 0.14 mmol) in 5 ml dichloromethane and 25 mg of copper-(I)-chloride and was stirred for about 50 minutes to 60 minutes under reflux in an argon atmosphere. The solvent was then removed under vacuum and the residue stirred in ethylacetate, filtered and evaporated again. The residue was purified by column chromatography (15% ethylacetate/cyclohexane). The catalyst (I) was obtained as a green solid.

The invention claimed is:
1. Compounds of formula (I)

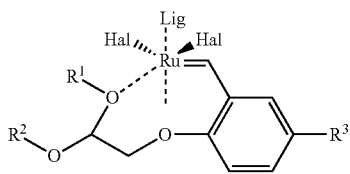

(I)

in which
Ru stands for ruthenium,
R1 stands for alkyl,
R2 stands for alkyl,
R3 stands for an electron-withdrawing substituent,
Hal stands for chlorine or bromine, independently of each other,
Lig stands for the ligand Lig1 or Lig2, wherein

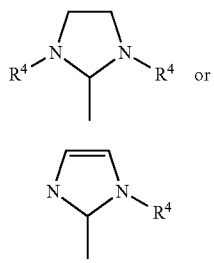

Lig1 or

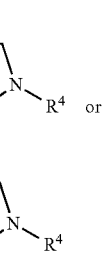

Lig2 and wherein R4 stands for mesityl.

2. The compounds of formula (I)

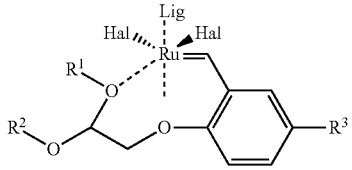

(I)

wherein
Ru is ruthenium,
R1 is methyl or ethyl,
R2 is $C_6$-$C_{18}$ alkyl,
R3 is hydrogen, $C_1$-$C_{18}$ alkyl, or an electron-withdrawing substituent from the series nitro and $SO_2N(C_1$-$C_{18}$ alkyl),
Hal is chlorine or bromine, independently of each other,
Lig is

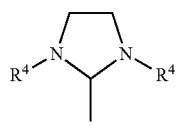

and wherein
R4 is mesityl.

* * * * *